United States Patent [19]

Gyllensten et al.

[11] Patent Number: 5,066,584
[45] Date of Patent: Nov. 19, 1991

[54] METHODS FOR GENERATING SINGLE STRANDED DNA BY THE POLYMERASE CHAIN REACTION

[75] Inventors: Ulf B. Gyllensten, Berkeley; Henry A. Erlich, Oakland, both of Calif.

[73] Assignee: Cetus Corporation, Emeryville, Calif.

[21] Appl. No.: 248,896

[22] Filed: Sep. 23, 1988

[51] Int. Cl.⁵ .............................................. C12P 19/34
[52] U.S. Cl. ......................................... 435/91; 935/17
[58] Field of Search ...................... 435/91, 6; 536/27; 436/63, 94; 935/17

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,889,818 | 12/1989 | Gelfand et al. | 435/194 |
| 4,965,188 | 10/1990 | Mullis et al. | 435/6 |

FOREIGN PATENT DOCUMENTS

| | | |
|---|---|---|
| 0258017 | 3/1898 | European Pat. Off. . |
| 0237362 | 9/1987 | European Pat. Off. . |

OTHER PUBLICATIONS

Fischer et al., Mar. 1983, *Proc. Natl. Acad. Sci. U.S.A.* 80:1579–1583.
Saiki et al., 20 Dec. 1985, *Science* 230:1350–1354.
Scharf et al., 5 Sep. 1986, *Science* 233:1076–1078.
Saiki et al., 13 Nov. 1986, *Nature* 324:163–166.
Wrischnik et al., 1987, *Nuc. Acids. Res.* 15(2):529–542.
Mullis et al., 1987, *Methods Enzymol.* 155:335–350.
Wong et al., 26 Nov. 1987, *Nature* 330:384–386.
Sakik et al., 29 Jan. 1988, *Science* 239:487–491.
Stoflet et al., 29 Jan. 1988, *Science* 239:491–494.
Scharf et al., May 1988, *Proc. Natl. Acad. Sci. U.S.A.* 85:3504–3508.
Horn et al., Aug. 1988, *Proc. Natl. Acad. Sci. U.S.A.* 85:6012–6016.
Gyllensten et al., Oct. 1988, *Proc. Natl. Acad. Sci. U.S.A.* 85:7652–7656.

*Primary Examiner*—James Martinell
*Attorney, Agent, or Firm*—Kevin R. Kaster

[57] ABSTRACT

Single stranded DNA can be generated by the polymerase chain reaction using two oligonucleotide primers, one persent in a limiting concentration. The single stranded DNA is useful in procedures involving utilizing nucleic acid probes and for purposes of nucleic acid sequencing.

7 Claims, 2 Drawing Sheets

METHODS FOR GENERATING SINGLE STRANDED DNA BY THE POLYMERASE CHAIN REACTION

BACKGROUND

1. Field of the Invention

Single stranded DNA plays a vital role in a number of different technologies. For instance, the determination of nucleic acid sequence has had an enormous impact in the fields of molecular biology, biochemistry, and genetics. Many sequencing protocols require utilization or generation of single stranded DNA at some stage of the process. The need for sequencing reagents and automated sequencing instruments has also created significant commercial activity. Single stranded nucleic acids are also used as probes in the emerging medical diagnostics technology based on hybridization of nucleic acids to detect pathogens and disease or disease-susceptible states. In addition, DNA "fingerprinting" techniques utilizing single stranded DNA probes has improved forensic methodologies.

2. Description of Related Disclosures

The present invention provides a method for generating single stranded DNA by the polymerase chain reaction (PCR). The PCR procedure involves repeated cycles of denaturation of the DNA, annealing of oligonucleotides primers to sequences flanking the segment of interest, and primer extension, typically mediated by a DNA polymerase, resulting in a doubling of the amount of a specific DNA fragment with each cycle. The PCR process requires a primer pair; the two primers define a segment of double stranded DNA that accumulates as the PCR product. The PCR process is described in U.S. Pat. No. 4,683,202 and results in a myriad number of identical copies of a double stranded DNA fragment.

PCR can be used to clone nucleic acid sequences never before identified or sequenced. The sequence of the PCR product can be identified either indirectly by hybridization to oligonucleotide probes, as described in U.S. Pat. No. 4,683,195, or directly by determination of the nucleotide sequence of the PCR amplified target. The sequence of DNA fragments generated by PCR has previously been determined either by cloning the fragments into derivatives of bacteriophage M13, as described by Scharf et al., 1986, *Science* 233:1076–1078, and Horn et al., 1988, *Proc. Natl. Acad. Sci. USA* 85:6012–6016 or by direct sequencing of the double stranded template, using a third "internal" primer, as described by Wong et al., 1987, *Nature* 330:384–386, and Wrischnik et al., 1987, *Nuc. Acids Res.* 15:529–535. However, the M13 cloning method is time consuming and requires that several sequences be determined to distinguish mutations occurring in the original sequence from i) random point mutations introduced by lack of fidelity of the DNA polymerase; and ii) artifacts such as the formation of mosaic alleles by in vitro recombination. Direct sequencing of double stranded templates can present difficulties due to the rapid reannealing of strands and the presence of sequences partially homologous to that of the sequencing primer on both strands, resulting in compound sequence ladders. These problems can be overcome by the method of the present invention to modify the PCR reaction in such a way that an excess of full length single stranded DNA of a chosen strand is produced that is suitable for sequence determination.

SUMMARY OF THE INVENTION

The present invention provides a method for generating single stranded DNA by the polymerase chain reaction. The method, termed "asymmetric PCR", comprises:

(a) treating a nucleic acid with deoxyribonucleoside-5'-triphosphates, an agent for polymerization, and a pair of oligonucleotide primers under hybridizing conditions such that an extension product of a first primer of said primer pair is synthesized that is complementary to a nucleotide sequence in said nucleic acid, wherein the extension product of said first primer can serve as a template for synthesis of an extension product of a second primer of said pair;

(b) denaturing the extension products of said primers formed in step (a) from the templates on which they were synthesized; and (c) treating the products of step (b) with the primers and under the conditions of step (a), wherein one of said first and second primers is present in limiting concentrations. The single stranded DNA generated in the reaction is the extension product of the primer present in the highest (not limiting) concentration during the reaction.

The present invention provides a number of significant advantages over known methods of producing single stranded DNA. The generation of single stranded DNA probes is a critical step in many important DNA sequencing methods and provides the basis for the diverse technologies that utilize nucleic acid probes and primers. The method is illustrated below in the direct sequencing of HLA DQα alleles in a heterozygote and for the generation of a nucleic acid probe. The present method has wide application in screening for and detecting mutations in genes and in facilitating automated DNA sequencing techniques.

BRIEF DESCRIPTION OF THE FIGURES

FIG. 1(a) shows the result with a primer pair using a ratio of primer one:primer two of 50:0.5 pmol up to 43 cycles. FIG. 1(b) shows the result with four different primer ratios: 50:50, 50:5, 50:0.5, and 50:0.05 pmol. The curves are based on densitometry scanning of autoradiographs.

DETAILED DESCRIPTION OF THE INVENTION

Figure 1:
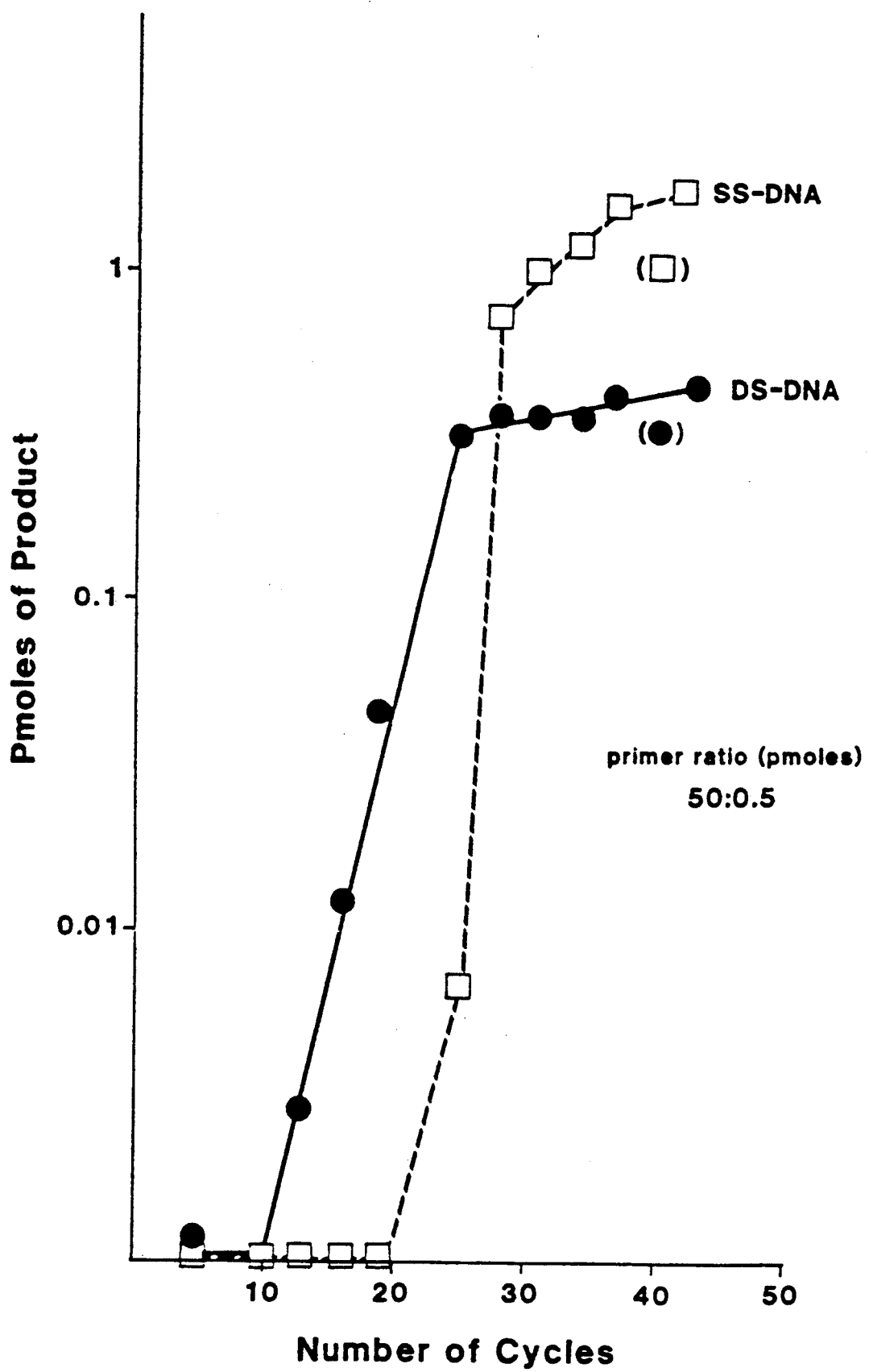
FIG. 1 depicts accumulation of double and single stranded DNA during a polymerase chain reaction at different primer ratios.
Figure 1:
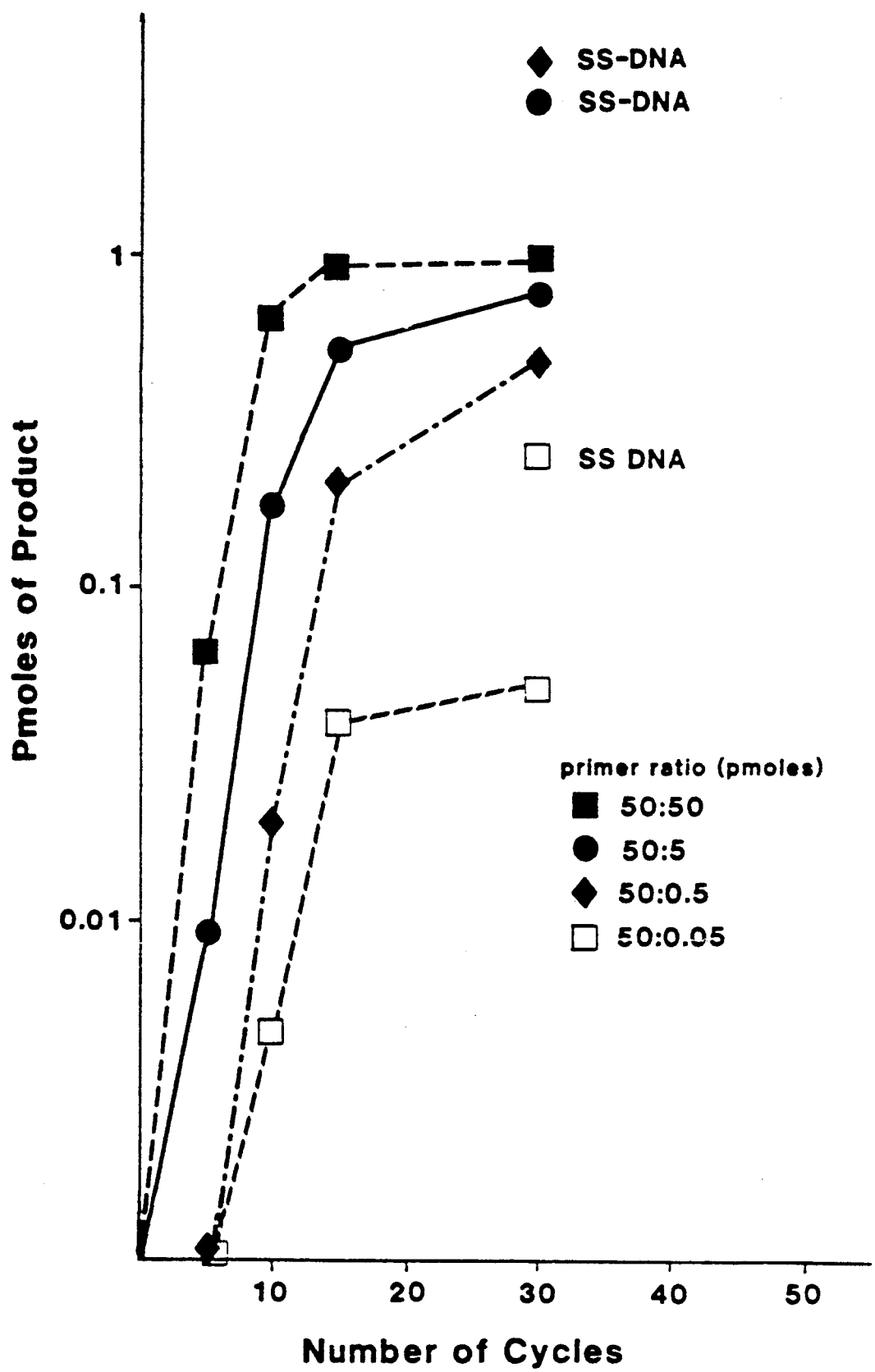

The present method for producing single stranded DNA by PCR requires that two amplication primers be present in different molar amounts.

The present invention provides a method for generating single stranded DNA by the polymerase chain reaction. The method, termed asymmetric PCR, comprises:

(a) treating a nucleic acid with deoxyribonucleaside-5'-triphosphates, an agent for polymerization, and a pair of oligonucleotide primers under hybridizing conditions such that an extension product of a first primer of said primer pair is synthesized that is complementary to a nucleotide sequence in said nucleic acid, wherein the extension product of said first primer can serve as a template for synthesis of an extension product of a second primer of said pair;

(b) denaturing the extension products of said primers formed in step (a) from the templates on which they were synthesized; and (c) treating the products of step (b) with the primers and under the conditions of step (a), wherein one of said first and second primers is present in limiting concentrations. The single stranded DNA generating in the reaction is the extension product of the primer present in the highest concentration during the reaction.

This method generates single stranded DNA by a modified PCR. The PCR process is described in U.S. Pat. Nos. 4,965,188; 4,683,195; and 4,683,202 and can employ the thermostable polymerase described in U.S. Pat. No. 4,889,818. The PCR process has been automated; an apparatus capable of carrying out the reaction is disclosed in related copending Ser. No. 899,061, filed Aug. 22, 1986, which is a continuation-in-part of abandoned Ser. No. 833,368, filed Feb. 25, 1986. Methods for the structure-independent amplification of DNA by a PCR with the structure-destabilizing base analog 7-deazaguanine are described in Ser. No. 248,556, filed Sept. 23, 1988. Methods for dideoxy-sequencing single-stranded DNA utilizing the thermostable DNA polymerase, called Taq polymerase, from *Thermus aquaticus* are described in Ser. No. 249,367, filed Sept. 23, 1988. The disclosures of these related applications and patents are incorporated herein by reference.

The invention can be illustrated by a reaction in which two primers are present: 50 pmol of primer one and 0.5 pmol of primer two. During the first cycles, when the primer in limiting concentrations is still present, predominantly double stranded DNA will be produced. However, when most or all of the primer present in limiting concentrations has been extended by the reaction, an excess of single stranded DNA, the extension product of the primer present in excess, will be produced in each cycle. If the reaction were 100% efficient, after about 0.5 pmol of double stranded DNA (dsDNA) has been generated, single stranded DNA (ssDNA) will start to accumulate at a rate of 0.5 pmol per cycle of amplification. The resulting ssDNA can be sequenced either by adding more of the amplification primer initially present in limiting amounts, or by using an internal primer complementary to the ssDNA.

Theoretically, the amount of dsDNA should increase exponentially, whereas the production of ssDNA should only follow a linear growth. It is therefore important that the production of dsDNA is allowed to reach a certain level before ssDNA production is initiated. The optimal point for initiating the generation of ssDNA is a few cycles before the reaction has reached the level at which the amount of enzyme present in the reaction limits the growth in copy number. The overall efficiency of amplification when one primer is limiting appears somewhat lower (70%) as compared to when both are present in vast excess (80–90%, see Saiki et. al., 1988 *Science* 239:487–491). In practice, this decreased efficiency can usually be compensated for by increasing the number of PCR cycles.

The accumulation of double stranded DNA (as determined by densitometry scanning of autoradiographs) appears to follow the pattern predicted above with a short exponential phase of increase followed by a phase of linear growth, as shown in FIG. 1(*a*). From the slope of the curve, the efficiency of amplification at various stages of the reaction can be calculated. During the exponential growth phase, the efficiency of accumulation of dsDNA is about 70%, while the efficiency of accumulation of ssDNA during the linear phase is only 30%. Practice of the present method with four different molar ratios of primers: 50:0.05, 50:0.5, 50:5, and 50:50 pmol, respectively, demonstrated that all three unequal molar ratios result in accumulation of ssDNA in amounts exceeding that of dsDNA after 30 cycles, as shown in FIG. 1(*b*). Surprisingly, with a primer ratio of 50:5, about 0.8 pmol of dsDNA and several pmol of ssDNA are produced after 30 cycles, indicating that ssDNA is produced even under conditions where the limiting primers is not exhausted (4 pmol remaining). This is probably due to the fact that the reaction has reached a level where the amount of enzyme available is insufficient to completely extend all the templates present during each cycle. Although the amount of ssDNA generated will vary between primer sets, a ratio of 1:50–1:100 will, after 30 cycles of PCR, generally produce a sufficient excess of ssDNA (1 to 5 pmol) for several sequencing reactions.

The ssDNA generated by the method can be sequenced using eithe the PCR primer that is limiting or an internal primer capable of annealing to the ssDNA and then applying conventional protocols for incorporation sequencing or labelled primer sequencing. The population of ssDNA strands produced should have discrete 5' ends but may be truncated at various close to the 3' end due to premature termination of extension. This 3'-end heterogenity will not affect sequencing of the ssDNA product, for only those ssDNA molecules that have been extended to include the sequence complementary to the sequencing primer will be utilized in the dideoxynucleotide sequencing reaction. Thus, the sequencing primer provides the discrete 5' end for the product of the sequencing reaction. When the PCR primer present in limiting amounts is used as the sequencing primer, only full length ssDNAs can serve as templates in the sequencing reaction.

The developmemt of a simple PCR protocol for generating specific single strands significantly facilitates the direct sequencing of the amplified product, as well as the preparation of hybridization probes. The rapid identification of new mutants or allelic variants can be accomplished by amplifying DNA segments using locus specific primers. Similarly, as Saiki et al., describe, the analysis of unknown sequences can be carried out by amplifying a cloned insert using vector specific primers that flank the insertion site. In both cases, a single-tube reaction method for producing single stranded PCR products could be linked to an automated sequencing system for rapid sequence determination. The present invention provides this important single-tube reaction method.

This direct sequence procedure is also capable of identifying both alleles in a heterozygous individual. The resolution of two alleles that differ by more than two nucleotides requires allele specific oligonucleotides (ASOs) that are capable of either priming the sequencing reaction in an allele-specific fashion or amplifying by PCR in an allele-specific manner. Alternative approaches to the problem of sequencing heterozygotes are to use restriction enzymes to cleave one of the two alleles, as described by Scharf et al., 1988, *Proc. Natl. Acad. Sci. USA* 85: 3534–3508, or to use denaturating gradient gels to resolve the allelic PCR products, as described by Fisher et al., 1983, *Proc. Natl. Acad. Sci. USA* 80: 1579–1583. One virtue of direct sequence analysis over cloning of PCR products in M13 is the simultaneous of both alleles.

For example, HLA typing can be greatly facilitated by the present method to detect both alleles simultaneously. An individual serologically typed as DQw3 could either be homozygous DQw3/DQw3 or DQw3/blank (there are some "blank" alleles which are not reactive with (i.e., typed by) existing serologic reagents). Direct sequence analysis could immediately reveal the "hidden" blank allele. However, using prior art methods, one would have to sequence several different M13 clones before being able to distinguish the two potential genotypes. Another advantage of the present direct sequencing method is that low frequency, erroneous PCR products will not interfere with sequence determination. Point mutations occuring due to lack of fidelity of the DNA polymerase will, even if they arise in the very first cycle of amplification, only represent at most 25% of the intensity of the nucleotides of the consensus sequence when, for example, chain termination reactions such as those described by Innis et al., Ser. No. 249,367, for DNA sequencing are analyzed by gel electrophoresis. Occasionally, mosaic alleles have been observed in PCR mixtures, presumably resulting from partially extended PCR products that can act as primers on other allelic templates in later cycles. Such products are likely to accumulate primarily in later cycles of the reaction because of insufficient enzyme to extend all available templates. Unless such recombinant alleles arise frequently, however, the consensus sequence remains readily recognizable.

When the method of the present invention is utilized in a direct PCR sequencing protocol, such as that described by Innis et al., the analysis of allelic variants at a known locus as well as the determination of unknown sequences can be greatly facilitated. In conjunction with such sequencing procedures, the present method provides for rapid and simple analysis of nucleotide sequences, with particular benefit to manufacturers of automated DNA sequencing instruments.

Thus, the present method was used to sequence the HLA DQα locus of several homozygous typing cell lines. The sequence ladder obtained showed that only a single template is generated in the PCR reaction. Given the extensive polymorphism of HLA genes, most individuals are heterozygous at these loci. Because these alleles differ at multiple positions including small deletions, direct sequencing of HLA variants will be feasible only if individual alleles can be distinquish without cloning them apart. This is possible using allele specific oligonucleotides (ASO) for either: (1) sequencing of only one allele at a time in a mixture; or (2) amplification of only one of the two alleles.

For example, when a DR1/DR3 heterozygote individual was sequenced with one of the DQα PCR primers, a compound sequence was generated. The two alleles differed at several positions close to the primer and at a 3 base pair (3 bp) deletion. The sequences obtained using oligonucleotides specific for the DQA1 and DQA4.1 alleles, respectively, as sequencing primers were identical to that of the two alleles of the DR1/DR3; DQA1/DQA4.1 heterozygote. In general, only one of the two alleles needs to be sequenced separately, because by "subtracting" this sequence from the heterozygote sequence, the other allele can usually be identified. For example, the two alleles of a DQA4.1/DQA3 individual differ by several nucleotide substitutions. Sequencing with a DQA4 ASO primer, one can identify one of the alleles, and the other allele can be subsequently reconstructed from the heterozygote sequence. It is also possible to use the ASOs to amplify selectively a specific allele in the heterozygote. These methods are suitable for sequencing alleles that are similar or identical to those previously described, but any difference between the ASO and the allele will be hidden and lost in the amplification. To identify the true genomic sequence to which the ASO anneals, a second oligonucleotide can be used as a sequencing primer.

The method of the present invention can also be used to generate radioactively labeled ssDNA, for use as a hybridization probe, as described in detail in Example 4. This aspect of the method of the invention was exemplified by amplifying a 242 bp segment of the HLA DQAα gene using primers flanking a hypervariable region. When the ratio of primer one to primer two was 50 pmol:0.5 pmol in PCR, the accumulation of product was observed over 43 cycles of amplification. A product of the expected size appeared, as detected by visibility on an ethidium bromide-stained gel, from about cycle 19. Under the conditions illustrated, accumulation appeared to stop at cycle 25. When a Southern blot of such a gel was probed with an internal oligonucleotide complementary to the ssDNA strand produced, the probe hybridized to the ssDNA band and a component with a lower molecular weight, corresponding to ssDNA. To confirm that the band represented ssDNA solely of one strand, the blot was stripped and reprobed with an oligonucleotide made to hyridize to the same strand as would the ssDNA. None of this probe hybridized to the band migrating at the molecular weight of ssDNA.

The above results were generated by using two oligonucleotide primers complementary to a central region of the 242 bp HLA DQAα fragment in the method of the invention. A plasmid containing DNA cloned from DQAα cDNA was used as the target nucleic acid. Thirty cycles of amplification were performed using three different molar ratios of primer one:primer two. These ratios were (a) 50:50, (b) 1:50 and (c) 50:1. The CPR reactions were performed in the presence of α-[$^{32}$P]dCTP. While reaction (a) only generated labeled dsDNA, both reactions (b) and (c) yielded ssDNA. The three amplifications were used as probes, without denaturation, to detect complementary sequences present in the product of a reaction analogous to reaction (b) but performed in the absence of radiolabeled nucleotide. Only the product of reaction (c) hybridized to both the ssDNA and dsDNA produced in the unlabeled (b) reaction. The product of reaction (b) only hybridized to the dsDNA, and the product of reaction (a) did not hybridize (as would be expected for undernatured dsDNA). These results demonstrate that the single stranded DNA produced by the present method is exclusively of one strand and can be utilized as a nucleic acid probe to detect specific nucleotide sequences.

Those skilled in the art recognize that the present method is suited to a variety of applications where the presence of single stranded DNA is desired. The present method is also preferred for use with other methodologies. For instance, the structure independent nucleic acid amplification method described by Innis et al. that utilizes 7-deaza-2'-deoxyguanosine-5'-triphosphate in PCR can also be used with the present method. The DNA sequencing method of Innis et al. can also be combined with the present invention to achieve a significant improvement over prior art methods. The following examples are provided merely to illustrate the invention and not to limit the scope of the accompanying claims.

EXAMPLE 1

Enzymatic Amplification of Genomic DNA

Genomic DNA (1 μg) was subjected to amplification with 2 units of the DNA polymerase from *Thermus aquaticus*, using conditions described in Saiki et al., 1988, *Science* 239:487–491, incorporated herein by reference. Thus, the reaction mixtures were in a volume of 100 μL and in a buffer composed of 50 mM KCl, 10 mM Tris-HCl (pH 8.4), 2.5 mM $MgCl_2$, each dNTP at 200 μM, and 200 μg/mL gelatin. The reaction mixture, including 50 pmol of primer GH26 (5'-GTGCTGCAGGTGTAAACTTGTACCAG) and 0.5 to 1 pmol of primer GH27 (5'-CACGGATCCG-GTAGCAGCGGTAGAGTTG) (Scharf et al., 1986, *Science* 233:1076–1078, incorporated herein by reference), were subjected to repeated PCR cycles of 30 seconds at 94° C., 1 minute at 55° C., and 2 minutes at 72° C. using a Perkin Elmer-Cetus Thermal Cycler. The reactions produced ssDNA complementary to a central region of the second exon of the DQα gene; the ssDNA produced was the extension product of the GH26 primer.

EXAMPLE 2

Electrophoretic Analysis of Amplifications

Aliquots of a reaction mixture prepared in substantial accordance with the procedure of Example 1 from successive cycles were dried down, resuspended in 5 μL of TE buffer, and electrophoresed through a 1% regular agarose, 3% NuSieve agarose gel for 2 hours at 5 volts/cm. Two μg of RF DNA from the phage φX174 cut with restriction enzyme HaeIII were used as a size standard. The agarose gel was then denatured for 45 minutes in a solution containing 0.4M NaOH and 1.5M NaCl, neutralized for 45 minutes in a solution containing 0.5M Tris-HCl, pH 7.5, and 1.5M NaCl, and the DNA transferred overnight in a solution of 4X SSC to a nylon filter (Genetran). The filter was baked for 1 hour at 80° C. in vacuum and prehybridized in a solution containing 5X SSPE, 5X Denhardt's solution, and 0.5% SDS for 15 minutes at 55° C.

Oligonucleotide probes specific for the DQα region were labeled with γ-$^{32}$P-ATP using T4 polynucleotide kinase. Unincorporated nucleotides were removed with the Centricon 30 microconcentrator (Amicon). Blots were hybridized in the same solution as that for the prehybridization, with addition of labeled oligonucleotide at a concentration of 0.1 pmol/mL, for 5 hours and then washed in 1X SSC at 42° C. for 30 minutes. The blots were exposed to Kodak X-omat film, and a number of different exposures were taken for densitometry scanning. The oligonucleotides were stripped off the blot by immersing the blot into distilled water at 60° C. for 15 minutes and prehybridized and rehybridized as above. This procedure, and the procedure of Example 1, modified as to primer ratios, was used to generate the data in FIGS. 1(*a*) and 1(*b*), which show accumulation of ssDNA and dsDNA in illustrative embodiments of the present invention as compared to when neither primer is present in limiting concentrations.

EXAMPLE 3

Sequencing of Single Stranded DNA

An entire amplification reaction (100 μL) produced in accordance with the procedure of Example 1 was mixed with 2 mL of distilled $H_2O$ and applied to the Centricon 30 microconcentrator, spun at 5,000 rpm to remove excess dNTPs and buffer components, and the retenate collected in a volume of 40 μL. About 10 μL of the retenate were dried down and resuspended in 9 μL of 1X sequencing buffer (40 mM Tris-HCl, pH 7.5; 20 mM $MgCl_2$; and 50 mM NaCl) and 1 μL of a solution containing 10 μM sequencing primer. This resulted in an approximate primer to template ratio of 10:1. After the primer/template mixture was heated at 65° C. for 5 minutes, the primer was annealed to the template by dropping the temperature to 30° C. over a twenty minute period. The solution was then made 10 mM in DTT and 75 nM with respect to each of dGTP, dCTP, and TTP. Five μCi of α-[$^{35}$S]dATP (1000 Ci/mmol) and 2 units of modified T7 DNA polymerase (Sequenase TM, U.S. Biochemicals) were also added. The labeling reaction (16 μL) was continued for 5 minutes at room temperature and then aliquoted to each of four tubes with 2.5 μL of termination mix (each with 80 μM of each dNTP to 8 μM of the appropriate ddNTP). After 5 minutes of incubation at 37° C., the reaction was stopped by adding 4 μL of a solution of 95% formamide and 20 mM EDTA, heated to 75° C. for 2 minutes and loaded onto a 0.4 mm thick, 6% polyacrylamide/7M urea gel. The gel was run at 40 mA, 1.8 kV for 2.5 hours, fixed in 10% glacial acetic acid/10% methanol for 10 minutes, dried, and exposed to Kodak X-omat TM film overnight. In general, this method produced sequencing ladders comparable to those generated using the same dideoxynucleotide sequencing procedure on single stranded M13 DNA.

EXAMPLE 4

Generation of Single Stranded Hybridization Probe

An 82 bp fragment, internal to the 242 bp HLA DQα product, was amplified using the primers GH84 and GH64. Fifty ng of a plasmid containing the DQα cDNA were subjected to 30 cycles of amplification using (a) 50 pmol of each primer, (b) 0.5 to 1.0 pmol of GH64 and 50 pmol of GH84, and (c) the reciprocal of (b). To obtain radiolabeled DNA, 5 μL of α-[$^{32}$P]dCTP (10μ Ci/μL, 1000 mCi/mmol) were added to the reaction, in addition to the nonradioactive nucleotides already present. Thus, during the amplification reaction by the present method (reactions (b) and (c)), ssDNA was generated that was labeled with $^{32}$P and could thus serve as a probe preparation without denaturation. After amplification, the unincorporated nucleotides were removed using a Centricon microconcentrator. Another amplification reaction, analogous to (b) but without radiolabeled nucleotide, was electrophoresed and transferred to triplicate nylon membranes. Reactions (a), (b), and (c) were used to hybridize against the three nylon membranes. The results of the hybridization, discussed above, demonstrate that the present method can be used to produce ssDNA probes.

Other modifications of the embodiments of the invention described above that are obvious to those of ordinary skill in the areas of nucleotide chemistry, molecular biology, biochemistry, nucleic acid probe diagnostic technology, and related disciplines are intended to be within the scope of the accompanying claims.

We claim:

1. A method for generating single stranded DNA by the polymerase chain reaction, said method comprising:
   (a) treating a nucleic acid with deoxyribonucleoside-5'-triphosphates, an agent for polymerization, and first and second oligonucleotide primers under hybridizing conditions such that an extension product of said first primer is synthesized that is complementary to a nucleotide sequence in said nucleic acid, wherein the extension product of said first primer can serve as a template for synthesis of an extension product of said second primer and the first primer is present in excess of the second primer;

(b) denaturing the extension products of said primers formed in step (a) from the templates on which they were synthesized;

(c) treating the products of step (b) with the primers and under the conditions of step (a); and (d) repeating steps (b) and (c) until said second primer is present in a limiting concentration so that the extension product of the first primer accumulates in excess of the extension product of the second primer.

2. The method of claim 1, wherein said agent for polymerization is *Thermus aquaticus* DNA polymerase.

3. The method of claim 1, wherein said primers are present in a ratio of first primer to second primer in the range of 10:1 to 1000:1.

4. The method of claim 1, wherein said primers are present in a ratio of first primer:second primer of 10:1.

5. The method of claim 1, wherein said primers are present in a ratio of first primer:second primer of 50:1.

6. The method of claim 1, wherein said primers are present in a ratio of first primer:second primer of 100:1.

7. The method of claim 1, wherein said primers are present in a ratio of first primer:second primer of 1000:1.

* * * * *

UNITED STATES PATENT AND TRADEMARK OFFICE
CERTIFICATE OF CORRECTION

PATENT NO. : 5,066,584

DATED : November 19, 1991

INVENTOR(S) : H. Erlich and U. Gyllensten

It is certified that error appears in the above-identified patent and that said Letters Patent is hereby corrected as shown below:

On the cover sheet, under the heading "ABSTRACT", line 3, delete "persent" and insert therefor --present--.

Column 4, line 19, delete "eithe" and insert therefor --either--.

Column 4, line 24, after "various" insert --points--.

Signed and Sealed this

Sixteenth Day of March, 1993

*Attest:*

STEPHEN G. KUNIN

*Attesting Officer*     *Acting Commissioner of Patents and Trademarks*